United States Patent [19]

Okazaki et al.

[11] Patent Number: 5,072,451
[45] Date of Patent: Dec. 10, 1991

[54] MOLECULAR CRYSTAL AND METHOD FOR CONVERTING LIGHT WAVELENGTH BY USE THEREOF

[75] Inventors: Masaki Okazaki; Makoto Ishihara; Koji Matsuo, all of Kanagawa, Japan

[73] Assignee: Fuji Photo Film Co., Ltd., Kanagawa, Japan

[21] Appl. No.: 642,759

[22] Filed: Jan. 18, 1991

[30] Foreign Application Priority Data

Jan. 19, 1990 [JP] Japan ................................. 2-10422

[51] Int. Cl.⁵ .......................... H01S 3/109; H03F 7/00
[52] U.S. Cl. ...................................... 372/22; 252/582; 252/587; 252/589; 548/227; 359/328
[58] Field of Search ................. 372/21, 27; 307/425, 307/427; 252/582, 587, 589; 548/227

[56] References Cited

U.S. PATENT DOCUMENTS

| | | | |
|---|---|---|---|
| 3,926,970 | 12/1975 | Sauter | 252/582 X |
| 4,120,971 | 10/1978 | Saari et al. | 424/272 |
| 4,559,147 | 12/1985 | Hirth et al. | 252/1 |
| 4,565,820 | 1/1986 | Schnur | 514/314 |
| 4,818,899 | 4/1989 | Tiers | 307/425 |
| 4,955,977 | 9/1990 | Dao et al. | 350/96.34 |
| 5,015,417 | 5/1991 | Clement et al. | 252/587 |

Primary Examiner—William L. Sikes
Assistant Examiner—Galen J. Hansen
Attorney, Agent, or Firm—Sughrue, Mion, Zinn, Macpeak & Seas

[57] ABSTRACT

A molecular crystal comprising a molecule represented by formula (I) shown below:

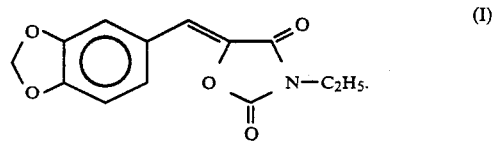

(I)

The crystal has high blue light transmittance and non-linear optical characteristics.

6 Claims, 2 Drawing Sheets

MOLECULAR CRYSTAL AND METHOD FOR CONVERTING LIGHT WAVELENGTH BY USE THEREOF

FIELD OF THE INVENTION

This invention relates to a molecular crystal useful as a non-linear optical material Also, it relates to a method for converting light to a different wavelength by use of the molecular crystal as the non-linear optical material.

BACKGROUND OF THE INVENTION

In recent years, non-linear optical materials have been attracting increasing attention. Under favorable conditions (e.g., high intensity, phase matching) they convert light of a given wavelength into light of a different wavelength. Non-linear optical devices have utilized the non-zero components of the second order polarizability tensor to achieve second harmonic generation, parametric amplification, the addition and subtraction of frequencies, modulation and the like of coherent electromagnetic reaction.

Such materials have been generally known as non-linear optical materials, and described in detail in references as mentioned below: "Nonlinear Optical Properties of Organic and Polymeric Material", ACS Symposium Series 233, edited by David J. Williams (published by American Chemical Society, 1983); "Yuki Hisenkei Kogaku Zairyo; Organic Non-linear Optical Material", supervised by Masao Kato, Hachiro Nakanishi (CMC, published in 1985); "Nonlinear Optical Properties of Organic Molecules and Crystals", vol. 1 and vol. 2, edited by D. S. Chemla and J. Zyss (published by Academic Press in 1987).

As one of the popular uses of non-linear optical materials, there is the wavelength converting device using second harmonic generation (SHG) or frequency doubling based on the non-linear effect and the addition of frequencies and the subtraction of frequencies.

Briefly, electromagnetic waves propagating in a crystal having non-linear optical properties induce polarization waves with frequencies which are the sum and the difference of the frequencies of the exciting waves. These polarization waves can radiate electromagnetic waves having the frequencies of the polarization waves. The energy transferred to a radiated electromagnetic wave from a polarization wave depends on the magnitude of the component of the second order polarizability tensor involved, since this tensor element determines the amplitude of the polarization wave and also depends on the distance over which the polarization wave and the radiated electromagnetic wave can remain sufficiently in phase, called the coherence length. Phase matching occurs when the waves are completely in phase.

Generally phase matching is of two types:
(i) Type I, wherein the two incident waves have the same polarizations; and
(ii) Type II, wherein the two incident waves have orthogonal polarization.

Phase matching can be achieved by "tuning" the crystal in various ways such as by rotation of the crystal to vary the refractive indices, by varying the temperature, by application of an electric field, or by compositional variation.

Those non-linear optical materials which have been used up to date are inorganic perovskites as represented by lithium niobate. Recently, however, π-electron conjugated system organic compounds having an electron donating group and an electron attracting group have been known to have various performances as the non-linear optical materials surpassing greatly those of the inorganic materials mentioned above.

For formation of non-linear optical materials having higher performances, compounds having higher non-linear sensitivities under molecular state are required to be aligned so as to give rise to no inverse symmetry. For atainment of high non-linear sensitivity, compounds with a long π-electron conjugated chain have been known to be useful, and described variously in the above-mentioned literatures. However, in those compounds, the absorption maximum wavelength will become longer as is self-evident, bringing about, for example, lowering in transmittance of blue light, which is an impediment against generation of blue light as the second harmonic. This also occurs in p-nitroaniline derivatives, and the great effect of the wavelength on efficiency of the second harmonic generation is apparent from Alain Azema et al, Proceedings of SPIE, vol. 400, New Optical Materials, 1983, p. 186, FIG. 4.

Therefore, it has been desired to have a nonlinear optical material with higher transmittance to blue light. In the prior art, investigations have been made involving replacement of the carbon atoms on the benzene nucleus of nitroaniline with nitrogen atoms, but no satisfactory result has been obtained.

Also, more excellent methods have been disclosed in JP-A-62-210430 (the term JP-A as used herein means an "unexamined published Japanese patent application") and JP-A-62-210432.

However, as described previously, to be useful as the secondary non-linear optical material, not only must the performance in the molecular state be sufficient, but it is essentially required that the molecular alignment under gathered state (i.e., incrystalline form) should have no inverse symmetry. It is extremely difficult to predict molecular alignment, and the probability for existence of satisfactory properties for any given organic compound is not high.

SUMMARY OF THE INVENTION

Accordingly, a first object of the present inveniton is to provide a molecular crystal having a molecular alignment having excellent blue light transmittance and also no inverse symmetry. A second object is to provide a method for conversion of light wavelength utilizing the non-linear response.

The present inventors have intensively studied, and consequently found that the objects of the present invention can be accomplished by a molecular crystal comprising a molecule represented by formula (I) shown below.

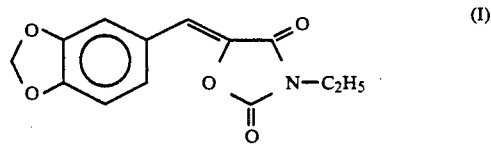

1: powder sample, 2: basic wave cut filter, 3: spectrophotometer, 4: photomultiplier, 5: amplifier, (11) wavelength 1,064 μm, (12): 0.532 μm.

Figure 3:
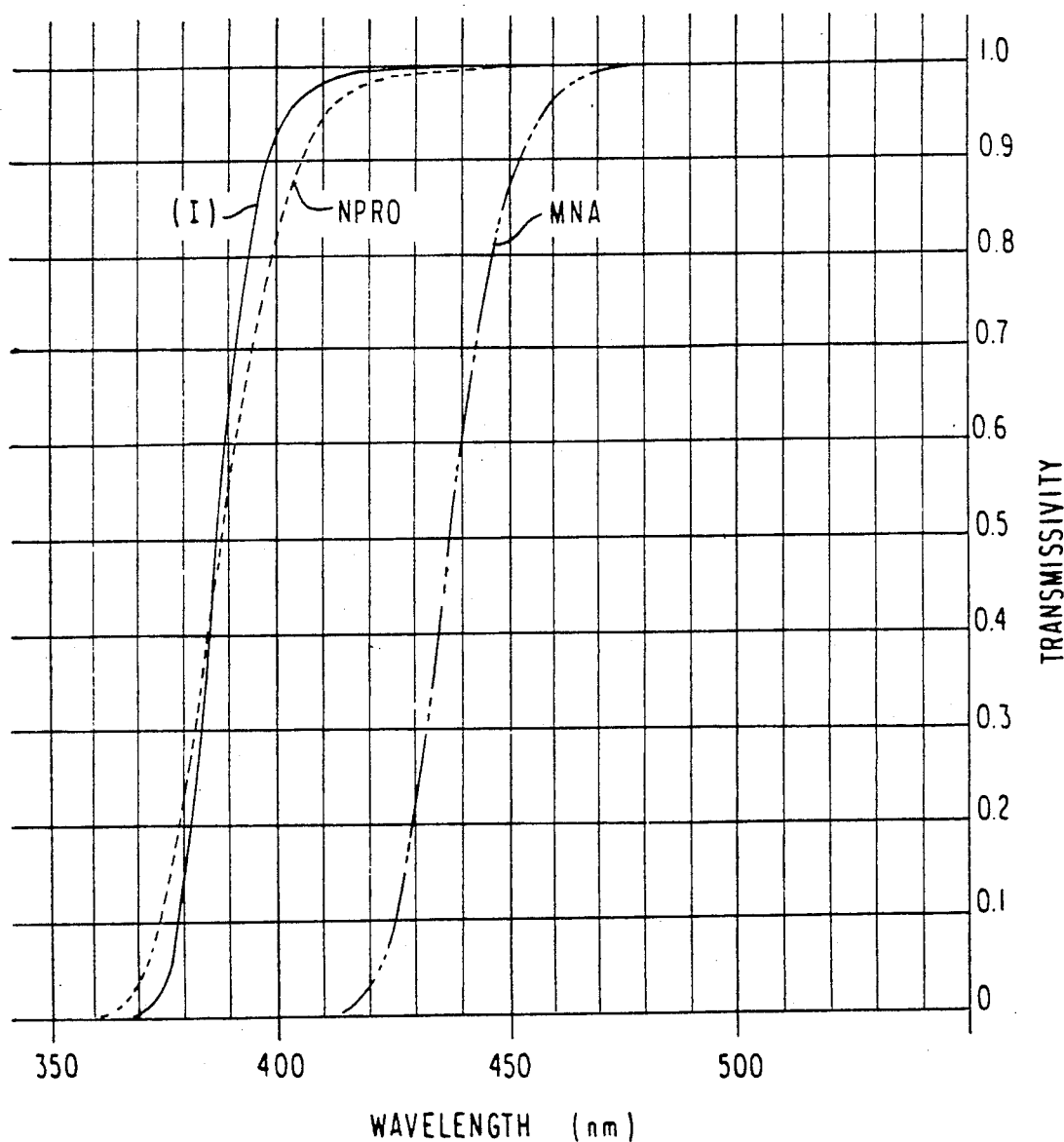

FIG. 3 shows wavelength vs transmissivity of the compound of formula (I), MNA, and NPRO.

DETAILED DESCRIPTION OF THE INVENTION

The compound of the formula (I) can be generally synthesized according to the method as described below.

That is, it can be obtained by the Knoevenagel reaction between piperonal and 3-ethyloxazolidine-2,4-dione. As the solvent, alcohols, ethers, nitriles, amides, etc. can be employed, and as the catalyst, acids or bases can be employed.

The reaction can be carried out at a temperature within the range from $-100°$ C. to $100°$ C., preferably from $-78°$ C. to $50°$ C.

An efficient way of obtaining second harmonic radiation from a laser is to place a crystal with non-linear properties inside the resonator cavity. The technique of intracavity second harmonic generation, as this is called, is described, e.g., in Geusic, J. E., et al., IEEE J. Quant. Elect. QE-4,352 (1968).

In the following, a synthesis example is shown.

SYNTHESIS EXAMPLE 1.16 g (7.73 mmol) of piperonal and 1.00 g (7.75 mmol) of N-ethyl-2,4-oxazolidinedione are introduced into a 50 ml of eggplant-shaped flask, and a spiral condenser and a drying tube are mounted thereon. The reaction vessel is internally charged with an atmosphere of nitrogen and about 10 ml of THF dried with molecular sieve is added, followed by dissolution by stirring with a magnetic stirrer. After dissolution, 0.36 g (9.0 mmol) of NaH (60 wt. %, oily) is added little by little under stirring with magnetic stirrer. After stirring at room temperature for 2 hours, the reaction mixture is poured into water. The oily substance formed is extracted with ethyl acetate, and after drying over magnesium sulfate, the solvent is removed under reduced pressure, followed by recrystallization from methanol to give 0.34 g (1.3 mmol) of N-ethyl-5-(3,4-methylenedioxy-benzylidene)-2,4-oxazolidinedione at a yield of 17 % (m.p.=135°-137 ° C.).

For elemental analysis, the product is further recrystallized according to the vaporization method from a solvent mixture of acetone-n-hexane before use (m.p.=139°-140° C.).

Elemental analysis:
Calcd. for $C_{13}H_{11}NO_5$:
C (%)=59.78, H (%)=4.24, N (%)=5.36;
Found:
C (%)=59.66, H (%)=4.12, N (%)=5.36.

It can be used as the wavelength converting device according to the methods as described below.

1. By single crystal formation of the above-described compound at the fiber portion of the fiber, a wavelength converting device by use of a glass as the clad material can be prepared, and a YAG laser beam can be inputted to generate its second harmonic. Further, as another method, a waveguide type wavelength converting device can be similarly prepared to generate the second harmonic. As the phase matching method at this time, the Cherenkoff radiation system may be employed. However, these are not limitative, but also waveguide-waveguide phase matching is possible. The wavelength converting wave is not limited to the second harmonic, but may be also used for generation of the third harmonic, the addition of frequencies, and the subtraction of frequencies.

2. Next, the above-described compound can be formed into a single crystal, wherefrom a bulk single crystal can be cut out and YAG laser beam can be inputted to generate its second harmonic. For the phase matching method at this time, angle phase matching may be employed. These bulk single crystals can be used not only outside of the cavity, but also within the cavity of the solid laser such as the LD excitation solid state laser, etc., whereby wavelength efficiency can be enhanced. Further, by arrangement of the external resonator type LD within the resonator, the wavelength conversion efficiency can be enhanced.

For the single crystal formation as described above, the Bridgeman method, the solvent vaporization method, etc. can be used.

A wavelength conversion wave is not limited to the second harmonic, but also for generation of the third harmonic, the addition of frequency, and the subtraction of frequencies.

The present invention is described in detail below by referring to Examples.

EXAMPLE 1

Figure 1:
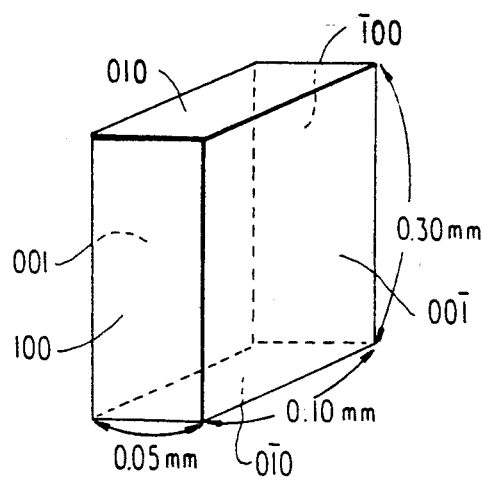
FIG. 1 shows the shape and the plane indicates of the single crystal prepared by the solvent vaporization method of an acetone solution (colorless transparent, elongated in the lb axis direction).
Figure 1:
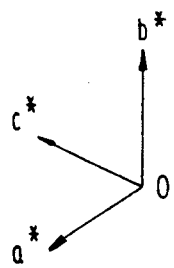

The compound of the formula (I) obtained according to the method as described above was dissolved in a solvent mixture of acetone/methanol=1/1, and colorless transparent plate crystals were obtained by the solvent vaporization method. The size was found to be $0.5 \times 0.4 \times 0.3$ mm. Also, colorless transparent columnar crystals of $0.05 \times 0.10 \times 0.30$ mm were obtained by the solvent vaporization method from acetone solution (FIG. 1).

The results of X-ray crystal structural analysis performed on the above crystals are shown below.

Crystallographic data:
Monoclinic system, Space group $P2_1$
Lattice constants, $a=7.160$ Å, $b=12.640$ Å, $c=13.591$ Å, $\beta=98.30°$, $V=1217.2$ Å$^3$
Molecule number per unit lattice $Z=4$.

From the above space group of the crystallographic data, it can be understood that the present crystal has no inverse symmetry.

As the method for single crystal formation, in addition to that as described above, the solution method such as the temperature drop method, the vapor diffusion method, the melted liquid method such as the Bridgeman method, and the method by sublimation may be employed.

The size of single crystal should be preferably 0.3 mm or more at the maximum side length.

EXAMPLE 2

Measurement of the second harmonic generation was conducted for the powder of the compound of the present invention according to the method described in S. K. Kurtz, T. T. Perry, Journal of Applied Physics (J. Appl. Phys.), vol. 39, p. 3798, 1968.

Figure 2:
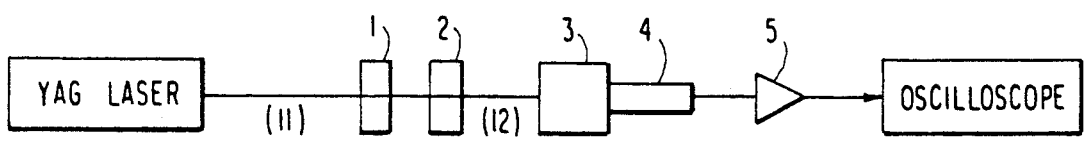
FIG. 2 shows the measuring device of the powder method, and the numerals in the drawing are defined below.

Measurement was carried out by the device shown in FIG. 2.

That is, measurement was carried out by use of a pulsed YAG laser beam ($\lambda = 1.064$ μm, beam diameter = about 1 mm $\phi$, peak power = about 10 Mw/cm$^2$) as the basic wave, and the intensity of its second harmonic was measured by the evaluation device shown in FIG. 2. Measurement was conducted by relative comparison with the intensity of the second harmonic of urea. When the intensity was weak, observation was performed visually. Particularly, for distinguishing emission by 2 photon absorptions of the basic wave (primarily yellow, red emissions) from the second harmonic, a spectrophotometer was introduced so as to measure only the second harmonic. Further, measurement by the powder method is intended primarily for judging presence of non-linearity of the substance, and its intensity ratio is a reference value for amplitude of nonlinearity.

The results are shown in Table 1.

TABLE 1

| Compound (relationship with the invention) | SHG efficiency | EtOH $\lambda_{max}$/nm | EtOH $\lambda_{cutoff}$/nm |
|---|---|---|---|
| Formula (I) (Invention) | 1 | 343 | 402 |
| MNA (Comparison) | 22 | 374 | 458 |
| NPRO (Comparison) | 9.6 | 327 | 410 |

In the Table, $\lambda_{cutoff}$ is a wavelength which shows a transmittance of 95% in an ethanolic solution of $4 \times 10^{-4}$ mol/liter. Thus, it is apparent that the compound of the present invention has excellent blue light transmittance.

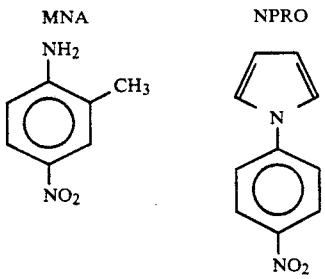

In addition, wavelength vs transmissivity ($4 \times 10^{-4}$ mol/liter EtOH) of the compound of formula (I), MNA, and NPRO is shown in FIG. 3.

REFERENCE EXAMPLE

The secondary non-linear optical constant ($\beta$) under the molecular state has been known to be calculatable on the basis of the calculation result according to the molecular orbital method, and has been known to be a useful indicator in molecular design. Table 2 shows the $\beta$ calculated on the basis of the PPP-CI method.

TABLE 2

Calculated value of (= 1.064)

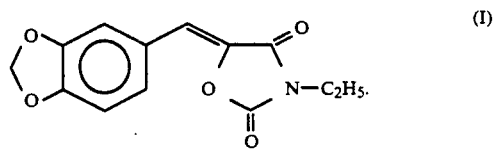

(Invention)

TABLE 2-continued

Calculated value of (= 1.064)

$22.42 \times 10^{-30}$ esu (Comparison)

$22.18 \times 10^{-30}$ esu (Comparison)

From Table 2, it can be clearly seen that the compound of the present invention is excellent.

As is apparent from Examples, the non-linear optical material of the present invention is particularly useful as the material for wavelength conversion. However, the uses of the non-linear material of the present invention are not limited to a wavelength converting device, but can be used for any element which utilizes the non-linear optical effect. Specific examples of the element for which the non-linear material of the present invention can be employed may include, besides the wavelength converting device, optical bistable devices (optical memory device, optical pulse wavelength control device, optical limiter, differential amplification device, optical transistor, A/D converting device, optical logic device, optical multi-vibrator, optical flip-flop circuit, etc.), optical modulation device and phase conjugation optical device, etc.

The crystal of the present invention has high blue light transmittance and non-linear optical characteristic as shown in Examples and Reference Example, and has been demonstrated to be useful for conversion of light wavelength, particularly for generation of blue light with the second harmonic.

While the invention has been described in detail and with reference to specific embodiments thereof, it will be apparent to one skilled in the art that various changes and modifications can be made therein without departing from the spirit and scope thereof.

What is claimed is:

1. A molecular crystal comprising a molecule represented by formula (I):

2. A method of generating coherent output optical radiation of an output wavelength, comprising directing at least one incident beam of electromagnetic radiation into a crystal, whereby electromagnetic radiation emerging from said crystal contains at least one frequency which is a second higher harmonic of the frequency of the incident beam of radiation, wherein said crystal is a single crystal comprising molecules represented by formula (I):

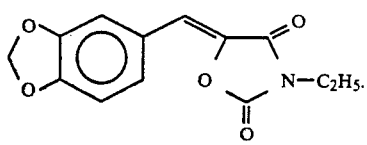
(I)

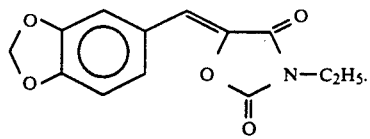
(I)

3. A non-linear optical device comprising a crystal having non-linear optical properties, and means for directing at least one incident beam of electromagnetic radiation into said crystal, whereby electromagnetic radiation emerging from said crystal contains at least one frequency different from the frequency of any incident beam of radiation, said crystal being a single crystal comprising molecules represented by formula (I):

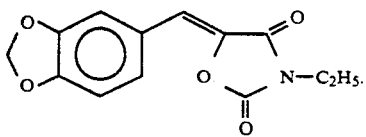
(I)

4. A Q-switched laser with YAG as gain medium having provided as an intracavity second harmonic generator a single crystal comprising molecules represented by formula (I):

5. An electrooptic modulator comprising means for directing a beam of polarized radiation into a birefringent crystal, and means for applying an electric field to said crystal to change birefringence, whereby the polarization of radiation emerging from said crystal is changed, wherein said birefringent crystal comprising molecules represented by formula (I):

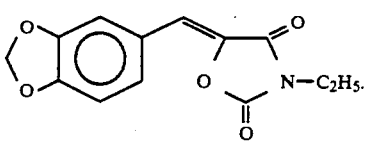
(I)

6. A crystal consisting essentially of molecules represented by formula (I):

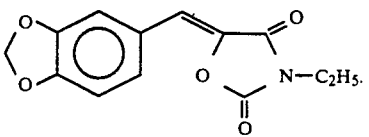
(I)

* * * * *